United States Patent
Kugler et al.

(10) Patent No.: US 10,398,391 B2
(45) Date of Patent: Sep. 3, 2019

(54) GENERATING A VOLUME IMAGE OF AN ELONGATED EXAMINATION OBJECT

(71) Applicants: Patrick Kugler, Erlangen (DE); Günter Lauritsch, Nürnberg (DE); Andreas Maier, Erlangen (DE)

(72) Inventors: Patrick Kugler, Erlangen (DE); Günter Lauritsch, Nürnberg (DE); Andreas Maier, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 221 days.

(21) Appl. No.: 15/351,850

(22) Filed: Nov. 15, 2016

(65) Prior Publication Data

US 2017/0135651 A1    May 18, 2017

(30) Foreign Application Priority Data

Nov. 16, 2015  (DE) .................. 10 2015 222 589

(51) Int. Cl.
*A61B 6/00* (2006.01)
*A61B 6/03* (2006.01)
(Continued)

(52) U.S. Cl.
CPC ............ *A61B 6/032* (2013.01); *A61B 6/027* (2013.01); *A61B 6/0407* (2013.01); *A61B 6/102* (2013.01);
(Continued)

(58) Field of Classification Search
CPC ..... A61B 6/027; A61B 6/5235; A61B 6/1014; A61B 6/482
See application file for complete search history.

(56) References Cited

U.S. PATENT DOCUMENTS 5,966,422 A * 10/1999 Dafni ............... A61B 6/032
378/15
7,020,235 B2  3/2006 Hornegger et al.
(Continued)

FOREIGN PATENT DOCUMENTS

DE  10241184 A1  4/2004
DE  102006040934 A1  3/2008

OTHER PUBLICATIONS

Computed Tomography Fundamentals, System Technology, Image Quality, Applications; Willi A. Kalender, Publics MCD Verlag; 2001.
(Continued)

*Primary Examiner* — Dani Fox
(74) *Attorney, Agent, or Firm* — Lempia Summerfield Katz LLC

(57) ABSTRACT

A tomography installation is configured to carry out a first scan along a first helix-segment-shaped trajectory section and to carry out a second scan along a second helix-segment-shaped trajectory section. A first data set is obtained during the first scan, and a second data set is obtained during the second scan. Taken by themselves in each case, both the first data set and the second data set are too incomplete for a reconstruction of a volume image without a partial revolution artifact. From the two data sets, a fused three- or four-dimensional data set is generated that is sufficiently complete for a reconstruction of a volume image without a partial revolution artifact.

16 Claims, 8 Drawing Sheets

(51) Int. Cl.
- *A61B 6/04* (2006.01)
- *A61B 6/02* (2006.01)
- *A61B 6/10* (2006.01)

(52) U.S. Cl.
CPC .......... *A61B 6/4014* (2013.01); *A61B 6/4441* (2013.01); *A61B 6/482* (2013.01); *A61B 6/5235* (2013.01)

(56) References Cited

U.S. PATENT DOCUMENTS

| | | | |
|---|---|---|---|
| 7,558,372 | B2 | 7/2009 | Zellerhoff |
| 2004/0066906 | A1 | 4/2004 | Hornegger et al. |
| 2008/0056438 | A1 | 3/2008 | Zellerhoff |
| 2017/0124732 | A1* | 5/2017 | Proksa .................. A61B 6/032 |

OTHER PUBLICATIONS

German office Action for related German Application No. 10 2015 222 589.5 dated Jul. 4, 2016, with English Translation.

Huh W., et.al: "Fast KVP-Switching Dual Energy CT for PET Attenuation Correction", in: IEEE Nuclear Science Symposium Conference Record, pp. 2510-2515, 2009.

Liu V., et al.: "X-ray micro-CT with a displaced detector array: Application to helical cone-beam reconstruction", in: Med.Phys., vol. 30, No. 10, pp. 2758-2761, Oct. 2003.

Rohkohl Christopher et al., "Improving best-phase image quality in cardiac CT by motion correction with MAM optimization", in: Medical Physics, vol. 40, No. 3, Mar. 2013, pp. 031901-1 til 031901-15.

Taguchi K., et.al.: "Modeling the performance of a photon counting x-ray detector: Energy response and pulse pileup effects", in: pp. 1-307.

Feldkamp, Lee A., L C. Davis, and James W. Kress. "Practical cone-beam algorithm." Josa a 1.6 (1984): pp. 612-619.

Manhart, M., Frank Dennerlein, and H. Kunze. "Online cone beam reconstruction with displaced flat panel detector." Proceedings of the First International Conference on Image Formation in X-Ray Computed Tomography, edited by Noo F., editor.(Salt Lake City, UT, 2010). 2010. pp. 1-4.

Yu, Z., et al. "First experimental results on long-object imaging using a reverse helical trajectory with a C-arm system." Proceedings of the second international conference on image formation in x-ray computed tomography. Salt Lake City, USA, 2012. pp. 364-368.

* cited by examiner

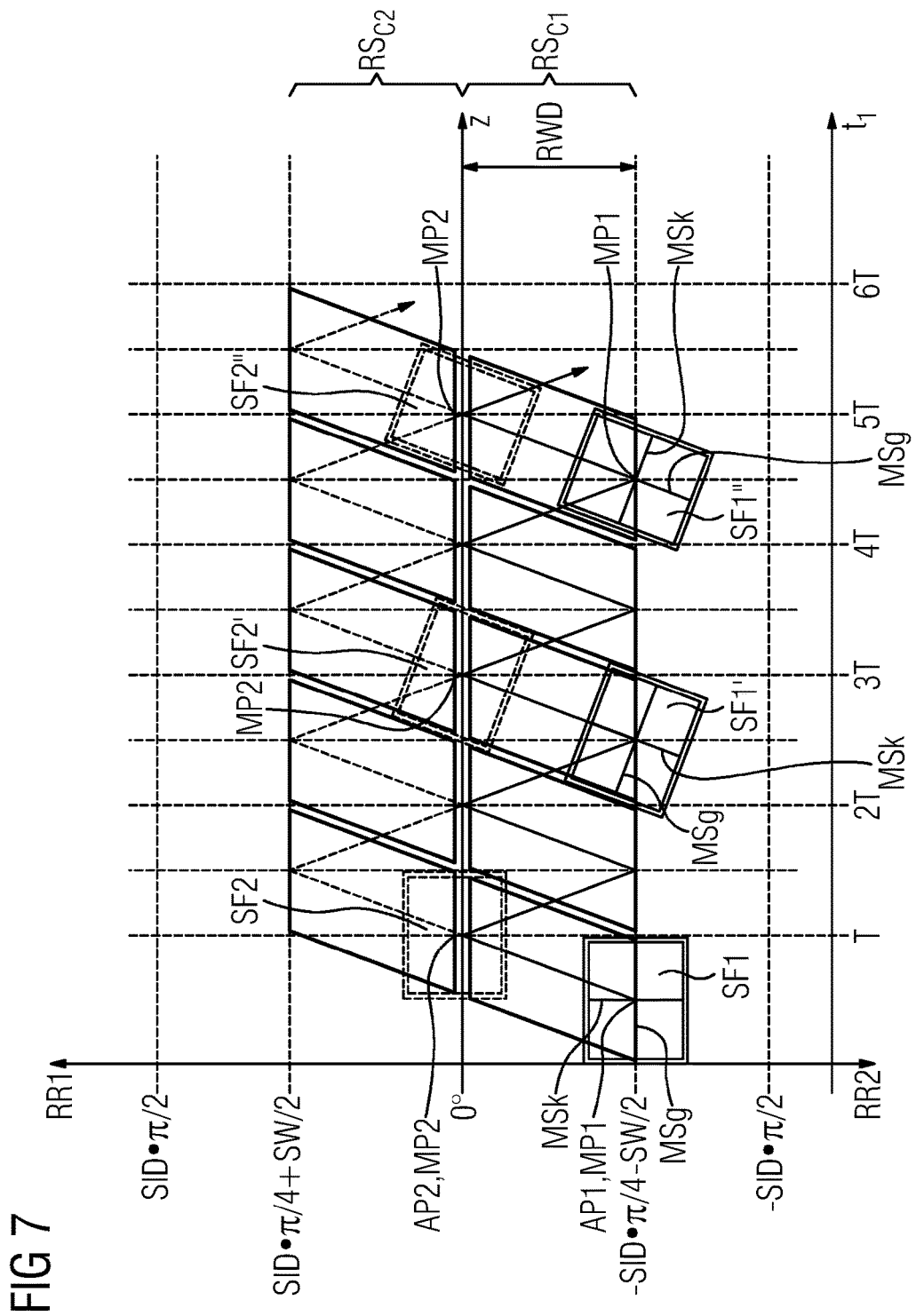

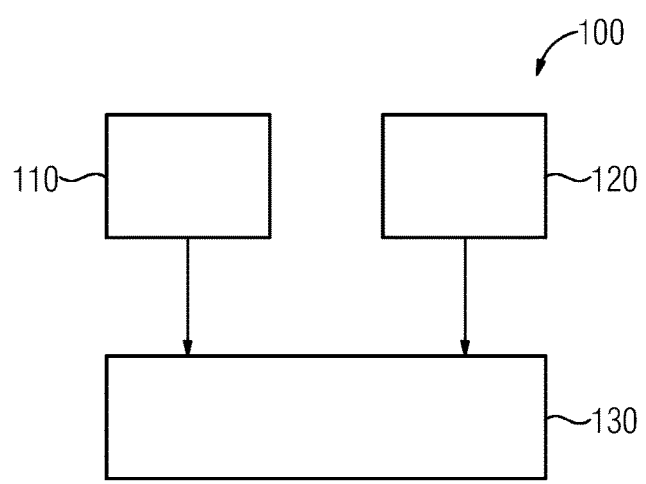

GENERATING A VOLUME IMAGE OF AN ELONGATED EXAMINATION OBJECT

CROSS-REFERENCE TO RELATED APPLICATIONS

This application claims the benefit of DE 10 2015 222 589.5, filed on Nov. 16, 2015, which is hereby incorporated by reference in its entirety.

TECHNICAL FIELD

Embodiments relate to a system and method for operating a tomography installation.

BACKGROUND

Embodiments relate to a tomography installation configured for performing a first scan along a first helix-segment-shaped trajectory section and a second scan along a second helix-segment-shaped trajectory section. A first data set is obtained during the first scan and a second data set is obtained during the second scan.

A data set is understood as a data set from a volume scan from which a complete three or four-dimensional volume image may be reconstructed. A data set of a volume scan includes the detected image data of the associated projection image for each projection angle used. A four-dimensional volume image may be a sequence of at least two three-dimensional volume images that succeed one another in time. A first volume image of the at least two three-dimensional volume images shows an influx phase, for example, and a second volume image of the at least two three-dimensional volume images shows, for example, an outflux phase. The tomography installation may be an x-ray tomography installation or a fluorescence tomography installation.

In diagnostics and therapy, stringent requirements are used for the performance of medical devices. The stringent requirements are in place for avoiding health hazards and personal injuries owing to erroneous diagnosis or treatment.

DE 10 2006 040 934 A1 describes a method for representing arteries and/or veins of a vascular system using a C-arm biplane system including two C-arms. During a fill run, for each C-arm a sequence of x-ray images is recorded from different projection angles. The x-ray images of the fill run from the first and second C-arms from an arterial phase are combined to form a first data set. The reconstruction to form a three-dimensional image data set may be carried out before the combination of the data of the x-ray images of the two C-arms or on the data set of the extracted arterial vascular system.

With known C-arm angiography systems it is not possible to capture a whole body or extensive parts of a body of an adult of normal size using a single scan trajectory. In known C-arm tomography installations, cable feeds for the C-arms limit the rotation angle range (about the orbital axis) of the beam source/detector pair of the respective C-arm to approximately 400°.

SUMMARY AND DESCRIPTION

Embodiments provide a tomography installation and a method for operating a tomography installation that overcome the design problem of conventional tomography installations.

In an embodiment, a tomography installation is configured for providing a first scan along a first helix-segment-shaped trajectory section and a second scan along a second helix-segment-shaped trajectory section. The tomography installation is configured for obtaining a first data set during the first scan and a second data set during the second scan and for generating from the two data sets a fused data set that is sufficiently complete for a reconstruction of a three- or four-dimensional volume image without a partial revolution artifact. Taken by themselves, both the first data set and the second data set are too incomplete for a reconstruction of a volume image without a partial revolution artifact.

An embodiment for operating a tomography installation includes the following actions. A first scan is carried out along a first helix segment shaped trajectory section. A second scan is carried out along a second helix-segment-shaped trajectory section. A first data set is obtained during the first scan and a second data set is obtained during the second scan. Both the first data set and the second data set are each too incomplete for a reconstruction of a volume image without a partial revolution artifact. From the two data sets a fused data set is generated that is sufficiently complete for a reconstruction of a three or four-dimensional volume image without a partial revolution artifact.

The tomography installation is configured for generating from the two data sets a fused data set that is sufficiently complete for a reconstruction of a three or four-dimensional volume image without a partial revolution artifact. Both the first data set and the second data set are each alone too incomplete for a reconstruction of a volume image without a partial revolution artifact. For the individual scans, each rotation angle range may be limited to 180° or to 100°, for example, without having to accept a partial revolution artifact. The rotation angle range allows for design advantages (in particular with regard to the cable feeds for each individual C-arm). A three- or four-dimensional image may be reconstructed from the fused data set using a reconstruction method (for example, a filtered back-projection method according to Feldkamp, Davis, Kress). The reconstructed image may be two-dimensional, three-dimensional, or four-dimensional. The dimensionality may be less than or equal to the dimensionality of the fused data set. Both trajectories may have an identical form (but with a rotation angle difference and/or an offset in the orbital axis direction). The second helix segment shaped trajectory may be arranged concentrically with respect to the first helix segment shaped trajectory. A radius of the first helix segment shaped trajectory may be of the same magnitude as a radius of the second helix segment shaped trajectory. The gradient of the helix segment shaped trajectories may be zero. In the degenerate case, the helix segment shaped trajectories may be circle segment shaped.

One embodiment provides for the first helix segment shaped trajectory section to extend over a first rotation angle range and the second helix segment shaped trajectory section to extend over a second rotation angle range. The sum of the first rotation angle range and the second rotation angle range is 360°. A minimum rotation angle position of the second helix segment shaped trajectory section is arranged in a manner offset by the first rotation angle range relative to a minimum rotation angle position of the first helix segment shaped trajectory section in the rotation direction. Alternatively, the minimum rotation angle position of the first helix segment shaped trajectory section may be arranged in a manner offset by the second rotation angle range relative to the minimum rotation angle position of the second helix segment shaped trajectory section in the rotation direction. From the data sets from two scans that were carried out over mutually complementary rotation angle ranges of 180°, a fused data set may be generated from which a complete volume image may be reconstructed without any partial revolution artifact.

Both scans may be performed as a large volume scan. In a large volume scan, a midpoint of a sensor surface of the detector is displaced relative to a central ray of the beam of the beam source by half a detector width in the rotation direction or opposite to the rotation direction. A diameter of the evaluatable recording region in the rotation direction is increased approximately by the factor of two.

A further embodiment provides for the first helix segment shaped trajectory section to extend over a first rotation angle range and the second helix segment shaped trajectory section to extend over a second rotation angle range RSC2. The first rotation angle range RSC1 is calculated as follows:

$$RS_{C1} = 180° + SW - RS_{C2}.$$

The second rotation angle range RSC2 is equal to or greater than half the magnitude of a width SW of a beam angle in the rotation direction. A minimum rotation angle position of the second helix segment shaped trajectory section is arranged in a manner offset by the first rotation angle range relative to a minimum rotation angle position of the first helix-segment-shaped trajectory section in the rotation direction. Alternatively, the minimum rotation angle position of the first helix segment shaped trajectory section is arranged in a manner offset by the second rotation angle range relative to the minimum rotation angle position of the second helix segment shaped trajectory section in the rotation direction. From the data sets from two scans that are carried out over mutually adjacent rotation angle ranges, a fused data set may be generated from which, as in a short scan, a complete volume image may be reconstructed without a partial revolution artifact. For a short scan, a midpoint of a sensor surface of the detector is arranged in a central ray of the beam of the beam source.

To carry out a large volume scan, the rotation angle ranges for the first scan and the second scan may be identical and may encompass in each case 90° plus half the beam angle. The sensor surface is displaced between the two scans in an opposite direction such that the midpoint of a sensor surface of the detector is displaced relative to a central ray of the beam of the beam source by half a detector width in the opposite direction.

The tomography installation is prepared for obtaining a first part of the second data set with a second radiation spectrum that is different than a first radiation spectrum used for obtaining a first part of the first data set. One embodiment provides for the first part of the first data set to include the entire first data set and for the first part of the second data set to include the entire second data set. An alternative embodiment provides for the tomography installation to be prepared for obtaining a remaining part of the first data set with the second radiation spectrum and a remaining part of the second data set with the first radiation spectrum. If the anode voltage and/or anode material used for generating the second radiation spectrum is different than that used for generating the first radiation spectrum, density measurements may be performed. The first data set may include the projection image data from two helix segment shaped trajectory sections, of which the first is traversed with the first radiation spectrum and the second is traversed with the second radiation spectrum. The second data set includes the projection image data from two helix segment shaped trajectory sections, of which the first is traversed with the second radiation spectrum and the second is traversed with the first radiation spectrum. By interchanging the data of the second helix segment shaped trajectory section between the two data sets, a first complete data set is obtained for the first radiation spectrum and a second complete data set is obtained for the second radiation spectrum.

The first data set may be recorded only on first helix-segment shaped trajectory sections that run in a first rotation direction. A small or a large midperpendicular of a first (rectangular) sensor surface of the first detector may be aligned parallel to the first helix segment shaped trajectory section, without the alignment needing to be changed during the step-by-step traversal of the helix turns. During the step-by-step traversal of the helix turns, the sensor surface does not need to be rotated about the central ray of the beam of the beam source in order that during the recording of the first data set, a yaw angle between the small or large midperpendicular of the first sensor surface and the first helix segment shaped trajectory section is zero degrees.

Alternatively, or additionally, the second data set is recorded only on second helix segment shaped trajectory sections that run in a rotation direction that is opposite to or in the same direction as the first rotation direction. If the first data set is obtained only on first helix segment shaped trajectory sections that run in a first rotation direction and the second data set is obtained only on second helix segment shaped trajectory sections that run in a rotation direction that is opposite to the first rotation direction, the first data set may be prevented from being influenced by a beam source provided for obtaining the second data set, and/or help to prevent the second data set from being influenced by a beam source provided for obtaining the first data set.

The first scan may be recorded if a midperpendicular of a first sensor surface of the first detector is aligned parallel to the first helix segment shaped trajectory section. Alternatively, or additionally, the second scan may be recorded if a midperpendicular of the second sensor surface of the second detector is aligned parallel to the second helix segment shaped trajectory section. As a result, the sensor surfaces are aligned such that the scan is optimal. An optimal use of the respective sensor surface may be achieved if the sensor surface of the respective detector has the form of a parallelogram whose internal angle is adapted to the gradient of the helix segment shaped trajectory section on which the associated beam source is active.

Independently thereof, the tomography installation may be prepared for carrying out the first scan if a midpoint of a sensor surface of the first detector is displaced relative to a central ray of a beam of the first beam source by half a detector width in the rotation direction or by half a detector width opposite to the rotation direction. Alternatively, the tomography installation may be prepared for carrying out the first scan if a midpoint of a sensor surface of the first detector is displaced relative to a central ray of a beam of the first beam source by half a detector width in a direction of the first helix segment shaped trajectory section. Each of these measures is suitable for increasing a diameter of an evaluatable recording region in the rotation direction.

Alternatively, or additionally, an expansion of the field of view in the rotation direction may also be achieved by a reduction of the source-to-image distance SID.

Depending on the tomography installation used, a minimum rotation angle position of the second helix segment shaped trajectory section is at a distance relative to a minimum rotation angle position of the first helix-segment shaped trajectory section in an orbital axis direction. The minimum rotation angle position may allow that an apparatus required for the first scan does not disturb (spatially obstruct) an apparatus required for the second scan, and/or that an apparatus required for the second scan does not disturb an apparatus required for the first scan. An obstruction may be relevant if the two scans (for example using a respective C-arm) are carried out synchronously in a biplane tomography installation.

The tomography installation may include for the first scan a first beam source and a first detector assigned to the first beam source, and includes for the second scan a second beam source and a second detector assigned to the second beam source. Typically, a distance between the first beam source and the first detector remains constant while the first detector is guided along the helix-segment-shaped first trajectory about the orbital axis which also applies to a distance between the second beam source and the second detector.

If the tomography installation is a monoplane tomography installation, the second scan is performed using the same detector as the first scan, specifically temporally before or after the first scan.

The first beam source (or second beam) and the first detector (or second detector) may be fixed to a common movable carrier, for example the same first C-arm, or to different movable carriers, for example each to a respective robot arm. Both beam source/detector pairs may be fixed to a common movable carrier, for example the same C-arm. An image intensifier may be connected to the first detector. An image intensifier may be connected to the second detector. The first detector may include an image intensifier and/or the second detector may include an image intensifier. A tomography installation including more than two beam sources may be used, for example a triplane or quadruplane tomography installation.

The scope of the present invention is defined solely by the appended claims and is not affected to any degree by the statements within this summary. The present embodiments may obviate one or more of the drawbacks or limitations in the related art.

BRIEF DESCRIPTION OF THE DRAWINGS

FIG. 7 depicts a further example scan of a biplane tomography installation.

FIG. 8 depicts an example method for operating a tomography installation.

DETAILED DESCRIPTION

Figure 1:
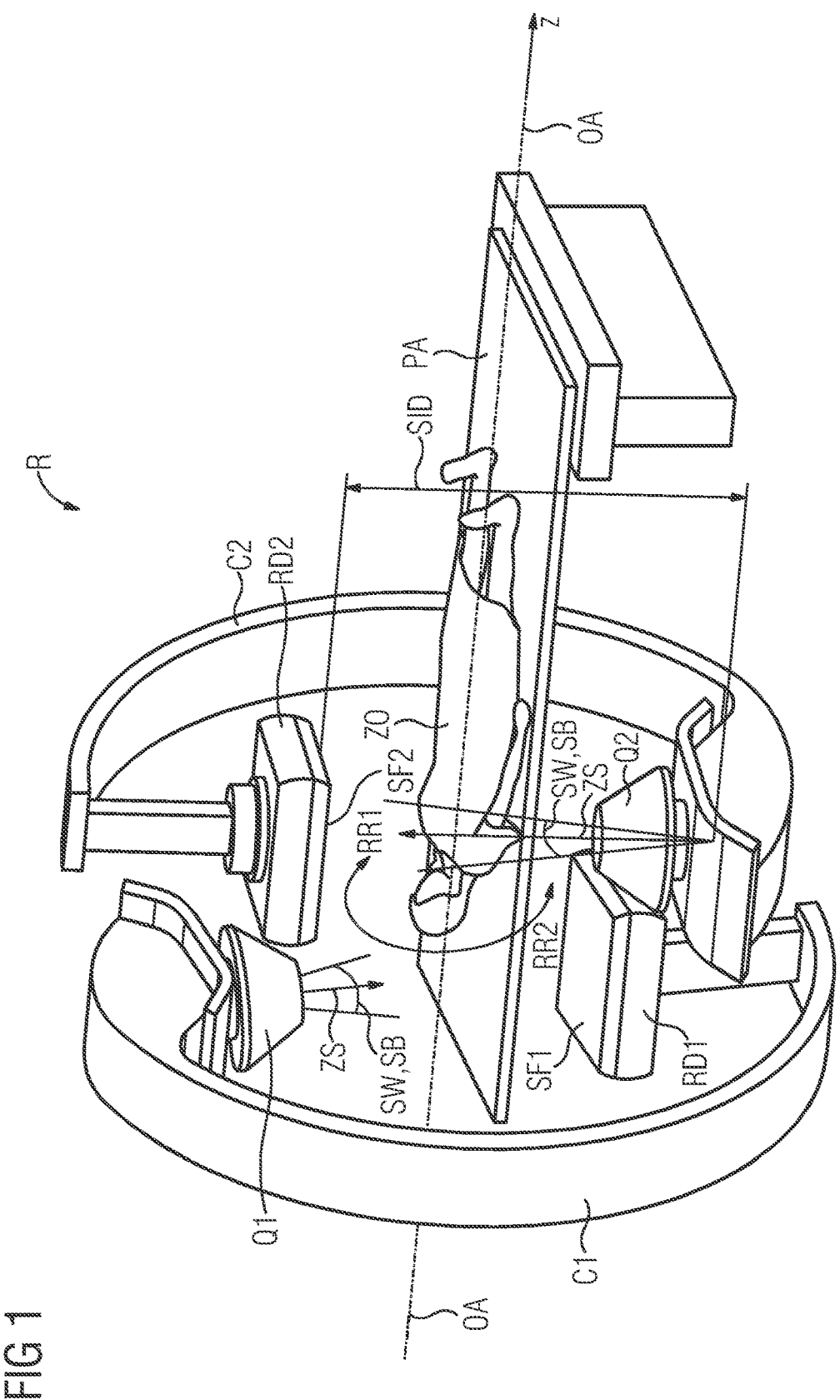
FIG. 1 depicts an example biplane tomography installation.

The biplane tomography installation R shown in FIG. 1 includes a first C-arm C1 and a second C-arm C2 and a patient couch PA. A first beam source Q1 and a first detector RD1 are fixed to the first C-arm C1. A second beam source Q2 and a second detector RD2 are fixed to the second C-arm C2. In order to carry out a comprehensive scan on an object ZO to be examined, the first C-arm C1 carries out an orbital rotation RO about an orbital axis OA, while the second C-arm C2 synchronously likewise performs an orbital rotation RO about the same orbital axis OA. At the same time, the patient couch PA is moved along the orbital axis OA. The patient couch PA is moved at a constant speed in the orbital axis direction z. During the orbital rotation RO of the first C-arm C1, the (imaginary) plane in which the first C-arm C1 is situated may remain unchanged. Similarly, the second C-arm C2 may remain unchanged. Alternatively, or additionally, both C-arms may be moved along the orbital axis OA during the scan. If the tomography installation R is a monoplane tomography installation, e.g. where only one C-arm C1 is present, the second scan is performed using the same detector RD1 as the first scan, temporally before or after the first scan. For alternative embodiments, the concepts and considerations applicable are the same as those known and/or described for a biplane tomography installation.

Figure 3:
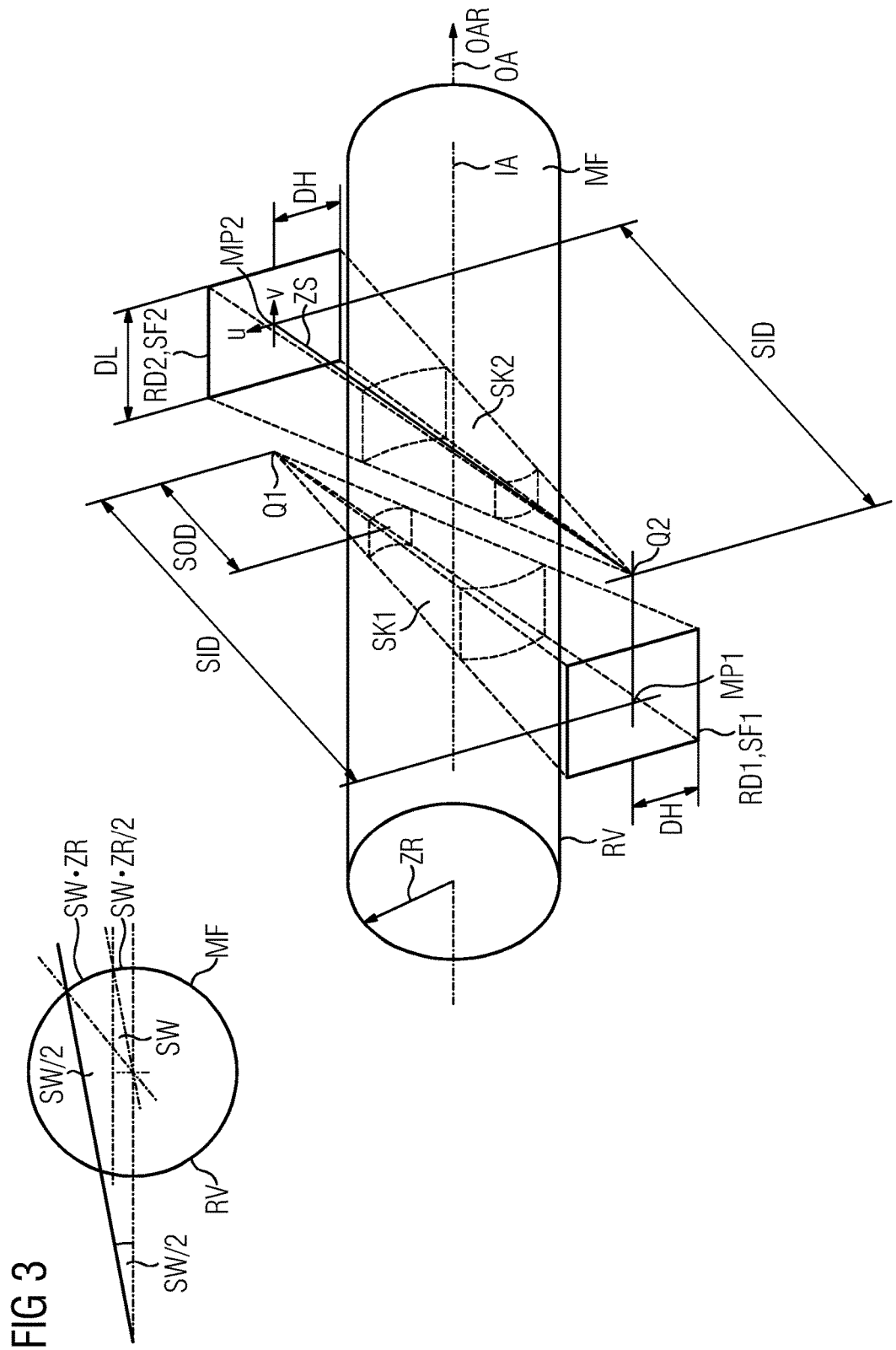
FIG. 3 depicts an example completely reconstructable volume using an arrangement of either two beam source/detector pairs or two positions of the same beam source/detector pair at two different points in time.

FIG. 3 depicts a first rotation angle range RSC1, in which the first detector RD1 is positionable, and a second rotation angle range RSC2, in which the second detector RD2 is positionable. The first detector RD1 carries out a zigzag movement over the entire first rotation angle range RSC1 of 180°. Whenever the first detector RD1 reaches one end or the other of the first rotation angle range RSC1, together with the beam source Q1 assigned to the first detector, the latter changes the rotation direction RR1, RR2. With regard to the object ZO to be examined, the first detector RD1 traverses helix-segment-shaped trajectory sections BA1 with an alternate rotation direction RR1, RR2. The same correspondingly holds true for the second detector RD2. Whenever the second detector RD2 reaches one end or the other of the second rotation angle range RSC2, together with the beam source Q2 assigned to the second detector, the latter changes the rotation direction RR1, RR2. Regarding the object ZO to be examined, the second detector RD2 also traverses helix-segment-shaped trajectory sections BA2 with an alternate rotation direction RR1, RR2.

Scans of arbitrary length are possible using a periodic juxtaposition of the helix-segment-shaped trajectory sections. Each of the two-beam source/detector pairs Q1/RD1, Q2/RD2 performs a respective zigzag movement over a rotation angle range RSC1 and RSC2, respectively. The beginning of the period T of the back and forth movement of the second beam source/detector pair Q2/RD2 may correspond to the beginning of the period of the back and forth movement of the first beam source/detector pair Q1/RD1 or (as shown in the example in FIG. 6) may be offset temporally by a fraction (for example a half) of the period T relative to the beginning of the period of the back and forth movement of the first beam source/detector pair Q1/RD1.

Figure 2:
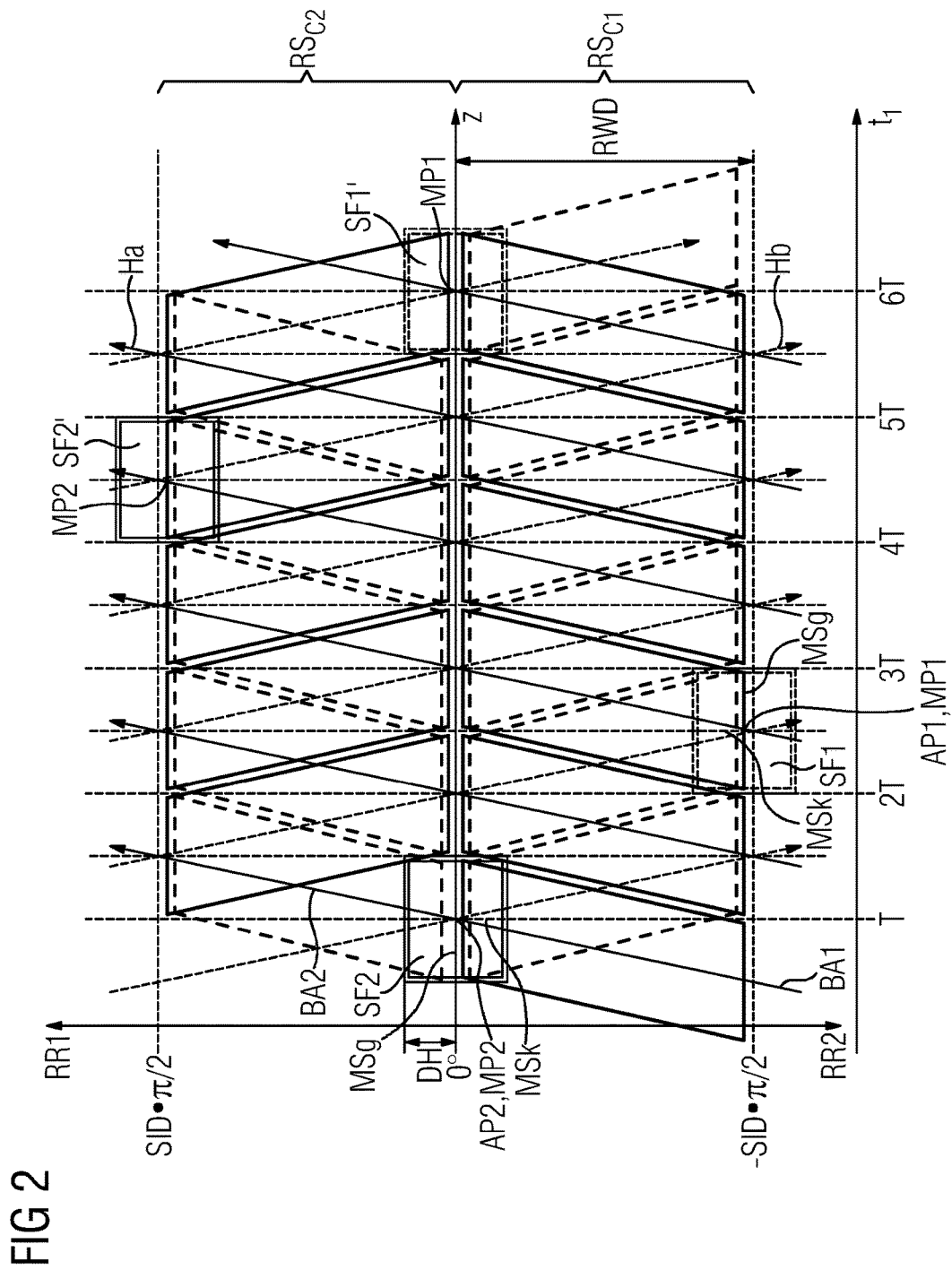
FIG. 2 depicts an example scan of a first embodiment of a biplane tomography installation.

In the embodiment in FIG. 2, the first beam source Q1 generates a first radiation spectrum in the first rotation direction RR1 and a second radiation spectrum in the second rotation direction RR2. The second beam source Q2 generates the first radiation spectrum in the second rotation direction RR2 and the second radiation spectrum in the first rotation direction RR1. In FIG. 2, scan sections in which the first radiation spectrum is used are framed by solid lines and scan sections in which the second radiation spectrum is used are framed by dashed lines. FIG. 2 illustrates that over the entire region that is scanned in the orbital axis direction z, over 360° each angle is scanned with the envisaged angular resolution (of 1°, for example) which applies both to the first radiation spectrum and to the second radiation spectrum.

Alternatively, a configuration that is not explicitly illustrated in FIGS. 2-7 is also possible in which the second beam source Q2 generates the first and second radiation spectrum in each case in the same rotation direction RR1, RR2 as the first beam source Q1, e.g. the first radiation spectrum in the first rotation direction RR1 and the second radiation spectrum in the second rotation direction RR2. For each of the two radiation spectrums over 360° each angle is scanned with the envisaged angular resolution (of 1°, for example) that applies to the entire region that is scanned in the orbital axis direction z.

FIG. 3 shows the boundaries of a completely reconstructable volume RV and an arrangement of two beam source/detector pairs Q1/RD1, Q2/RD2 of a biplane tomography installation R and the pyramidal beam cones SK1, SK2 thereof. The arrangement may also be regarded as positions of an individual beam source/detector pair Q1/RD1 at two different points in time. The first beam cone SK1 intersects the lateral surface MF of the completely reconstructable volume RV both on the entrance side and on the exit side.

As depicted by the corresponding angles theorem and the central angle theorem, the exit surface AF in the rotation direction RR1 is three times as wide as the entrance surface EF. The extension of the exit surface AF in the orbital axis direction OAR is calculated as $4*ZR.\sin(SW/2)$, wherein ZR denotes the cylinder radius of the completely reconstructable volume RV. In the embodiment depicted in FIG. 3, the isocenter lies on an isoaxis IA corresponding to the orbital axis of the tomography installation R and to the axis of symmetry of the cylindrical completely reconstructable volume RV. Depending on the embodiment, the difference in the dimensions of entrance surface EF and exit surface AF may be considered in the configuration of a scan scheme. In order to avoid a partial revolution artifact, with the envisaged angular resolution (of 1°, for example) over a rotation angle range of at least 180° each location of the lateral surface MF is irradiated by the beam cone SK1, SK2 of at least one of the two beam source/detector pairs Q1, Q2 in at least one position of the beam source/detector pair Q1/RD1, Q2/RD2. The rotation angle range may also be non-continuous, wherein diametrically opposite rotation angle positions may not be counted doubly, but rather only singly.

Figure 4:
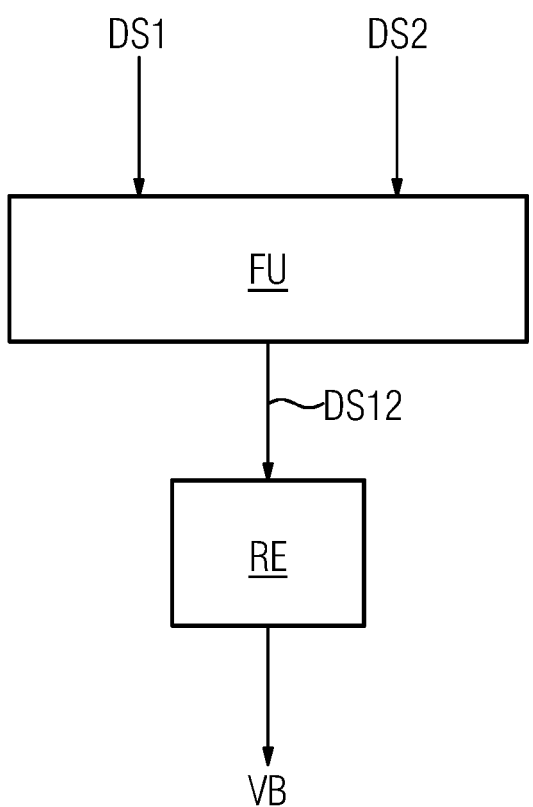
FIG. 4 depicts an example data flow of a tomography installation.

FIG. 4 shows a fusion unit FU for generating a fused data set DS12 from the first data set DS1 and the second data set DS2, and a reconstructor RE for generating a three- or four-dimensional volume image VB. In the simplest case, the fusion unit FU serves for a purely aggregative union of the first data set DS1 and the second data set DS2 (for example using a union interrogation). The reconstructor RE generates the three- or four-dimensional volume image VB from the fused data set DS12 using a known reconstruction method (for example using a filtered back-projection method according to Feldkamp, Davis, Kress).

Figure 5:
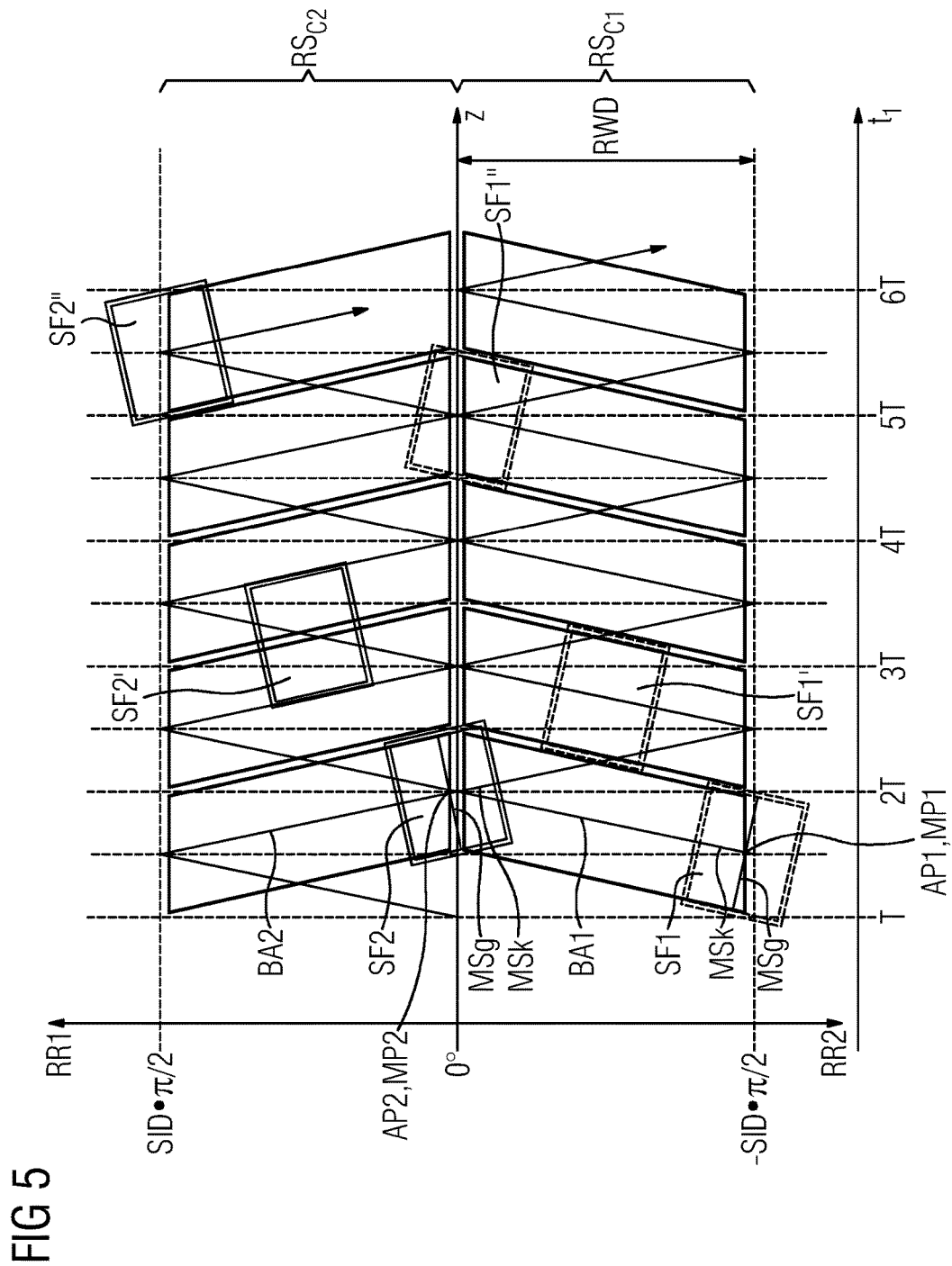
FIG. 5 depicts an example scan of a biplane tomography installation.

In the embodiment in FIG. 5, both beam source/detector pairs synchronously carry out zigzag movements over a rotation angle range of 180° in each case. However, here the first beam source Q1 is active only in a first rotation direction RR1 and the second beam source Q2 is active only in a second rotation direction RR2, that is opposite to the first rotation direction RR1.

In an embodiment, both beam source/detector pairs may synchronously carry out zigzag movements over a rotation angle range of 180° in each case, wherein both beam sources Q1, Q2 are active in the same rotation direction RR1 or RR2.

FIG. 5 depicts that over the entire region that is scanned in the orbital axis direction z, over 360° each angle is scanned with the envisaged angular resolution (of 1°, for example). The same radiation spectrum may be used.

The respective detector may remain in a position in which a small MSk or a large MSg midperpendicular of the (rectangular) sensor surface SF1, SF2 of the respective detector is aligned with (the gradient of) the helix-segment-shaped trajectory sections BA1 during such time periods in which the beam source Q1, Q2 assigned to it is active (e.g. along the "advancing" trajectory sections). The alignment of a midperpendicular MSk, MSg of the sensor surface SF1, SF2 with (the gradient of) the helix-segment-shaped trajectory sections BA1 makes it possible to avoid an unnecessary overlap of adjacent scan sections and thus to improve a dose efficiency and to optimize the acquisition speed. If the beam sources Q1, Q2 are inactive (e.g. along the "returning" trajectory sections), the respective detector RD1, RD2 is not required for data acquisition, e.g. may remain rotated about the central ray ZS in a manner such as is expedient for the subsequent data acquisition along the "advancing" trajectory sections.

Figure 6:
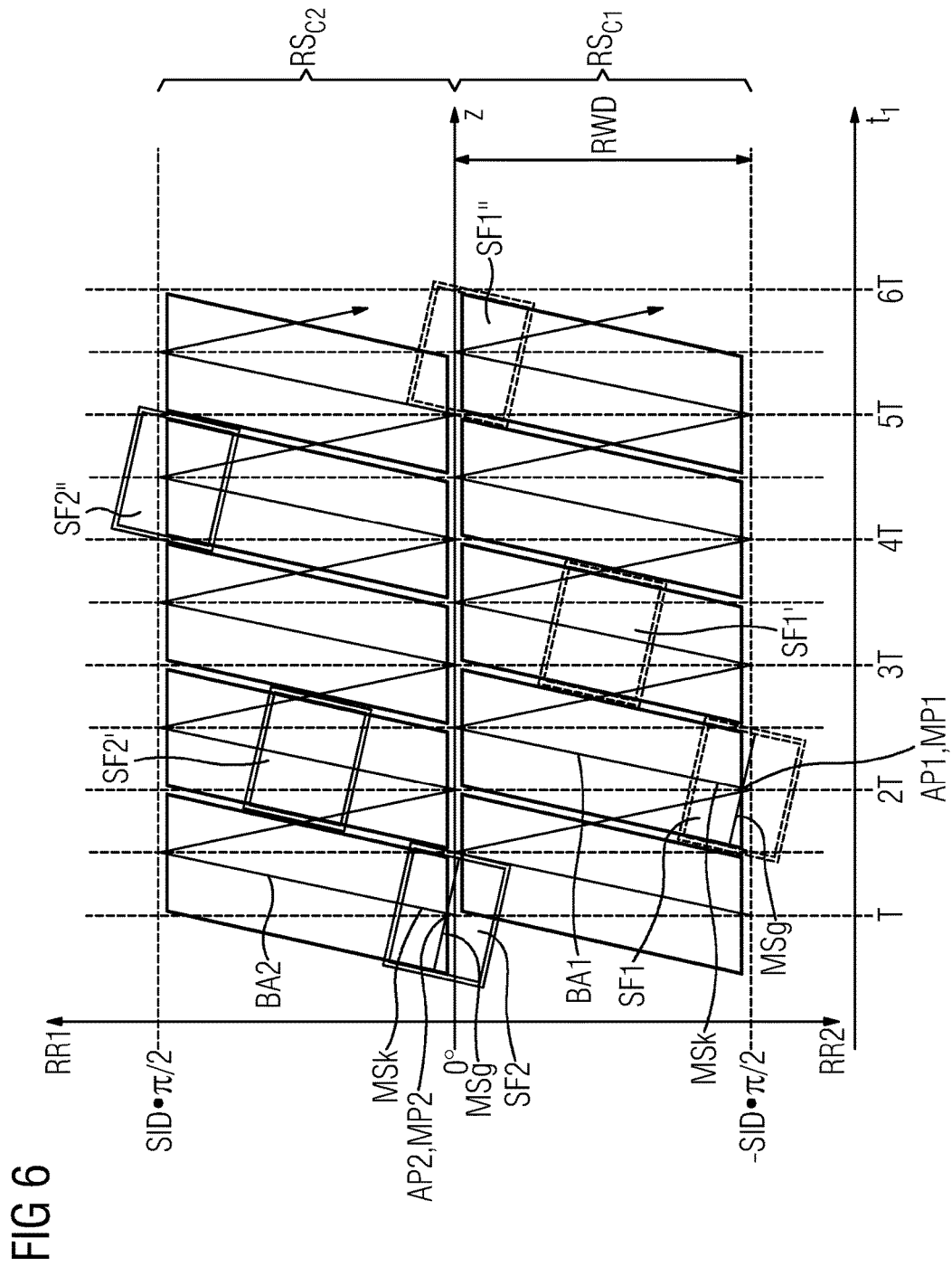
FIG. 6 depicts a further example scan of a biplane tomography installation.

In the embodiment in FIG. 6, the two-beam source/detector pairs synchronously carry out zigzag movements over a rotation angle range RSC1, RSC2 of 180° in each case. Here both beam sources Q1, Q2 are active in a first rotation direction RR1, while both beam sources Q1, Q2 are inactive in a second rotation direction RR2, that is opposite to the first rotation direction RR1. The figure shows that over the entire region that is scanned in the orbital axis direction z, over 360° each angle is scanned with the envisaged angular resolution (of 1°, for example). The same radiation spectrum may be used. For the embodiment in FIG. 6, the offset of the beginning of the period T of the back and forth movement of the second beam source/detector pair Q2/RD2 relative to the beginning of the period of the back and forth movement of the first beam source/detector pair Q1/RD1 is optional.

FIG. 7 depicts an embodiment with a fused helix short scan. Each of the two beam source/detector pairs carries out zigzag movements over a rotation angle range of ½, (180°+ SW). SW denotes a beam angle of the beam sources Q1, Q2. If partial revolution artifacts are intended to be avoided in a short scan for all locations (pixels, voxels), that lie within a convex envelope of the trajectory, the entire rotation angle of the central rays ZS of the two radiation sources Q1, Q2 for each of the locations is at least 180° plus the beam angle (in the rotation plane, e.g. perpendicular to the orbital axis). The beam angle may also be designated as fan angle. If the beam angle is 20°, for example, each of the two rotation angle ranges RSC1, RSC2 has a width IRSC1I, IRSC2I of 100°. Both beam sources Q1, Q2 are active in a first rotation direction RR1, but inactive in a second rotation direction RR2, that is opposite to the first rotation direction RR1. For the embodiment in FIG. 7, the shown rotation of the detector RD1, RD2 about the central ray ZS is optional.

The figure shows that over the entire region that is scanned in the orbital axis direction z, over 180° plus the beam angle SW of 20°, for example, each angle is scanned with the envisaged angular resolution (of 1°, for example). The same radiation spectrum may be used.

In all embodiments, the scan may be carried out with a monoplane installation or with a biplane installation R. If the scan is carried out with a monoplane installation the helix-segment-shaped trajectory sections BA1 of the first rotation angle range RSC1 may be scanned in a first work operation and the helix-segment-shaped trajectory sections BA2 of the second rotation angle range RSC2 may be scanned in a second work operation (for example during retraction of the patient couch PA).

The method 100 for operating a tomography installation R as illustrated in FIG. 8 includes the following actions. A first scan is carried out along a first helix-segment-shaped trajectory section BA1 and a second scan is carried out along a second helix-segment-shaped trajectory section BA2. A first data set DS1 is obtained during the first scan and a second data set DS2 is obtained during the second scan. Taken by themselves in each case, both the first data set DS1 and the second data set DS2 are too incomplete for a reconstruction of a volume image VB without a partial revolution artifact. From the two data sets DS1, DS2 a fused data set DS12 is obtained that is sufficiently complete for a reconstruction of a three- or four-dimensional volume image VB without a partial revolution artifact.

Embodiments include a new trajectory that enables a helix acquisition using a biplane system R. Scans of arbitrary length become possible using a juxtaposition of helix-segment-shaped trajectory sections (depicted in FIGS. 2 and 5 to 7). The acquisition may be combined with one or more displacements of the detector or detectors RD1, RD2, such that a diameter of the reconstructable region is doubled to double the magnitude. Volume images VB of volumes of arbitrary length may thus be generated using a monoplane or biplane C-arm tomography installation R.

One embodiment of the method 100 provides for both planes of a biplane tomography installation R to be rotated synchronously in order, taken together, to achieve a continuous helix acquisition. The two planes repeatedly rotate forward and backward synchronously. Each individual plane scans a reverse helix, the rotation angle range RSC1, RSC2 of which is limited, which results in a double scan includes two helices Ha, Hb with a mutually opposite winding direction (mutually opposite rotation sense). The data acquired by the double scan enables a fast and dose-efficient acquisition and generation of a volume image VB using known reconstruction algorithms.

Dual energy scans may thus also be realized by setting different anode voltages for both planes and, at the turning points of the respective trajectory, interchanging the anode voltages of the beam sources Q1, Q2 (at least in terms of value) between the planes which results in two complete helices H1, H2 for a respective anode voltage. For interchanging the anode voltages in terms of value, the following alternatives exist: changing the voltage of a voltage source that is (fixedly) assigned to the respective beam source Q1, Q2; interchanging the assignment of the two voltage sources to the two beam sources Q1, Q2 using an intermediate switch; and/or interchanging the assignment of the two beam sources (C-arms) to the two planes.

To avoid a self-collision, the two planes may be arranged offset in the rotation direction RR1, RR2 and/or along the orbital axis direction z. Alternatively, the trajectory may also be realized by monoplane systems, by recording the two partial trajectories successively.

In some embodiments of the tomography installation R, parts of the object ZO to be examined are recorded redundantly by the double scan. The redundancy may be used to achieve, for example, one or a combination of the following aims: reducing noise, compensating for movements, determining density information by switching over one or more radiation parameters (for example for generating a complete dual-source tomogram), and/or increasing a spacing (pitch) of the helix turns (for example from 22.5 cm to 45 cm). The same radiation intensity enables a faster advance. A recording time may be reduced and a dose efficiency may be improved.

The advance may be brought about optionally by the movement of the object ZO to be examined (for example using the patient couch PA) and/or by the movement of the beam source/detector pairs Q1/RD1, Q2/RD2 in the orbital axis direction OAR (or in the opposite direction).

Using the method 100, a volume image VB is generatable that, along the entire volume and at a distance of 5 cm from the isocenter, has a data coverage of 100% and is thus comparable with conventional helix recordings. In contrast to the conventional helix recording, the data coverage is provided up to a spacing of the helix turns of 45 cm. A shorter recording duration and thus lower dose are possible. In the case of a conventional helix recording, the spacing of the helix turns is 22.5 cm.

A detector height DL of 30 cm, a source-to-detector distance SID of 1200 mm and a source-to-object distance SOD of 600 mm may be assumed, wherein the detector height DL is the width of the sensor surface SF1, SF2 in the direction of the orbital axis OA. The direction OA may be designated as v-direction (if the detector is in the portrait mode or in the landscape mode, e.g. is not rotated about the beam axis).

From the intercept theorem, the width $h_{ISO}$ of a cone beam on the isoaxis IA with which the sensor surface SF1, SF2 still just detects over its entire detector height DL is calculated as follows:

$$h_{ISO} = DL \cdot SOD/SID.$$

Correspondingly, for the width $w_{ISO}$ of a cone beam perpendicular to the isoaxis IA with which the sensor surface SF1, SF2 still just detects over its entire width 2 DH in the rotation direction RR1, RR2 it follows that: $w_{ISO} = 2DH \cdot SOD/SID$ (wherein DH is half the width of the sensor surface in the rotation direction RR1, RR2). If a short scan is not involved, all voxels on the isoaxis IA are detected twice with a rotation by 360° resulting in a maximum gradient of the helix-segment-shaped trajectory BK1, BK2 of $2 \cdot h_{ISO}$. However, only half the volume to be reconstructed would thus be scanned. For a complete reconstructability, it is necessary to correct the maximum advance (the gradient) of the helix-segment-shaped trajectory BK1, BK2 by the radius $w_{ISO}/2$ of the volume as follows:

$$P_{helix} = 2*h_{ISO} - w_{ISO}/2 = (2DL - DH)SOD/SID.$$

For these parameters, the following results for the maximum helix advance given SOD/SID=0.5:

$$P_{helix} \approx 2*15 \text{ cm} - \frac{20 \text{ cm}}{2} = 20 \text{ cm}.$$

With the dimensions chosen, the maximum advance $P_{helix}$ is calculated as 20 cm rather than as 22.5 cm, as was ascertained in the numerical simulation. The deviation is unsurprising since the above formula for $P_{helix}$ is an estimation based on simplifications. The following advance may be chosen for the proposed double helix:

$$P_{helix} = 2P_{helix}$$

Embodiments provide for the first time to generate a three- or four-dimensional volume image of a volume of arbitrary length using a C-arm angiography system. The acquisition here is carried out on zigzag trajectories that are composed of helix-segment-shaped trajectory sections (BA1 and BA2, respectively) and that may be of arbitrary length in the orbital axis direction z. A three-dimensional volume image VB (without a partial revolution artifact) may be generated of an adult of normal size in one work operation. The three-dimensional volume image VB (without a partial revolution artifact) is not possible with known C-arm systems. Since the acquisition may be resorted with respect to at least one non-reverse complete helix Ha, Hb, it is possible to apply all reconstruction methods (e.g. all known and/or exact reconstruction methods) that are suitable for computed tomography which applies, for example, to spiral CT and helical CT methods. In addition, it is possible to shorten a recording time, to improve a dose efficiency and/or to apply dual-energy methods.

Embodiments relate to a tomography installation R prepared for the following: carrying out a first scan along a first helix-segment-shaped trajectory section BA1 and a second scan along a second helix-segment-shaped trajectory section BA2. A first data set DS1 is obtained during the first scan and a second data set DS2 is obtained during the second scan and from the two data sets DS1, DS2 a fused three- or four-dimensional data set DS12 is generated that is sufficiently complete for a reconstruction of a volume image VB without a partial revolution artifact. Taken by themselves in each case, both the first data set DS1 and the second data set DS2 are too incomplete for a reconstruction of a volume image VB without a partial revolution artifact.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A tomography device comprising:
one or more sources and one or more detectors configured to:
carry out a first scan along a first helix-segment-shaped trajectory section and a second scan along a second helix-segment-shaped trajectory section; and
obtain a first data set during the first scan and a second data set during the second scan,
wherein the tomography device is configured to generate from the first data set and the second data set a fused data set that is sufficiently complete for a reconstruction of a three- or four-dimensional volume image without a partial revolution artifact, and
wherein the first data set and the second data set, alone, are too incomplete for a reconstruction of a volume image without a partial revolution artifact.

2. The tomography device of claim 1, wherein the first helix-segment-shaped trajectory section extends over a first rotation angle range and the second helix-segment-shaped trajectory section extends over a second rotation angle range,
wherein a sum of the first rotation angle range and the second rotation angle range is 360°, and
wherein a minimum rotation angle position of the second helix-segment-shaped trajectory section is arranged in a manner offset by the first rotation angle range relative to a minimum rotation angle position of the first helix-segment-shaped trajectory section in the rotation direction, or wherein the minimum rotation angle position of the first helix-segment-shaped trajectory section is arranged in a manner offset by the second rotation angle range relative to the minimum rotation angle position of the second helix-segment-shaped trajectory section in the rotation direction.

3. The tomography device of claim 1, wherein the first helix-segment-shaped trajectory section extends over a first rotation angle range and the second helix-segment-shaped trajectory section extends over a second rotation angle range, and
wherein the first rotation angle range ($RS_{C1}$) is calculated as follows:

$$RS_{C1}=180°+SW-RS_{C2},$$

wherein the second rotation angle range ($RS_{C2}$) is at least half the magnitude of a width (SW) of a beam angle in a rotation direction, and wherein a minimum rotation angle position of the second helix-segment-shaped trajectory section is arranged in a manner offset by the first rotation angle range relative to a minimum rotation angle position of the first helix-segment-shaped trajectory section in the rotation direction, or wherein the minimum rotation angle position of the first helix-segment-shaped trajectory section is arranged in a manner offset by the second rotation angle range relative to the minimum rotation angle position of the second helix-segment-shaped trajectory section in the rotation direction.

4. The tomography device of claim 1, wherein the tomography device is further configured to obtain a first part of the second data set with a second radiation spectrum that is different than a first radiation spectrum used for obtaining a first part of the first data set.

5. The tomography device of claim 1, wherein the tomography device is further configured to record the first data set only on first helix-segment-shaped trajectory sections that run in a first rotation direction, record the second data set only on second helix-segment-shaped trajectory sections that run in a rotation direction that is opposite to or in the same direction as the first rotation direction, or record the first data set only on first helix-segment-shaped trajectory sections that run in the first rotation direction and the second data set only on second helix-segment-shaped trajectory sections that run in the rotation direction that is opposite to or in the same direction as the first rotation direction.

6. The tomography device of claim 1, wherein the tomography device is further configured to activate a first beam source of the one or more sources when a midperpendicular of a first sensor surface of a first detector of the one or more detectors is aligned parallel to the first helix-segment-shaped trajectory section, to activate a second beam source of the one or more beam sources when a midperpendicular of a second sensor surface of a second detector of the one or more detectors is aligned parallel to the second helix-segment-shaped trajectory section.

7. The tomography device of claim 1, wherein the tomography device is further configured to carry out the first scan when a midpoint of a sensor surface of a first detector of the one or more detectors is displaced relative to a central ray of a beam of a first beam source of the one or more sources by half a detector width in a rotation direction or by half a detector width opposite to the rotation direction, to carry out the first scan when a midpoint of a sensor surface of the first detector is displaced relative to a central ray of a beam of the first beam source by half a detector width in a direction of the first helix-segment-shaped trajectory section, or to carry out the first scan when the midpoint of the sensor of the first detector is displaced relative to the central ray of the beam of the first beam source by half the detector width in the rotation direction or by half the detector width opposite to the rotation direction and carry out the first scan when the midpoint of the sensor surface of the first detector is displaced relative to the central ray of the beam of the first beam source by half the detector width in the direction of the first helix segment shaped trajectory section.

8. The tomography device of claim 1, wherein a minimum rotation angle position of the second helix-segment-shaped trajectory section is at a distance relative to a minimum rotation angle position of the first helix-segment-shaped trajectory section in an orbital axis direction.

9. The tomography device of claim 1, wherein the one or more sources comprise a first beam source and a second beam source,
wherein the one or more detectors comprise a first detector assigned to the first beam source and a second detector assigned to the second beam source, and
wherein the first beam source and first detector are configured to carry out the first scan and the second beam source and second detector are configured to carry out the second scan.

10. A method for operating a tomography device, the method comprising:
performing a first scan along a first helix-segment-shaped trajectory section;
performing a second scan along a second helix-segment-shaped trajectory section;
obtaining a first data set during the first scan;
obtaining a second data set during the second scan, wherein each of the first data set and the second data set, alone, is too incomplete for a reconstruction of a volume image without a partial revolution artifact; and
generating a fused three- or four-dimensional data set from the first data set and the second data set, the fused three- or four-dimensional data set being sufficiently complete for a reconstruction of the volume image without the partial revolution artifact.

11. The method of claim 10, wherein the first helix-segment-shaped trajectory section extends over a first rotation angle range and the second helix-segment-shaped trajectory section extends over a second rotation angle range,
wherein a sum of the first rotation angle range and the second rotation angle range is 360°, and
wherein a minimum rotation angle position of the second helix-segment-shaped trajectory section is arranged in a manner offset by the first rotation angle range relative to a minimum rotation angle position of the first helix-segment-shaped trajectory section in the rotation direction, or
wherein the minimum rotation angle position of the first helix-segment-shaped trajectory section is arranged in a manner offset by the second rotation angle range relative to the minimum rotation angle position of the second helix-segment-shaped trajectory section in the rotation direction.

12. The method of claim 10, wherein the first helix-segment-shaped trajectory section extends over a first rotation angle range and the second helix-segment-shaped trajectory section extends over a second rotation angle range, wherein the first rotation angle range ($RS_{C1}$) is calculated as follows:

$$RS_{C1}=180°+SW-RS_{C2},$$

wherein the second rotation angle range ($RS_{C2}$) is at least half the magnitude of a width (SW) of a beam angle in the rotation direction, and
wherein a minimum rotation angle position of the second helix-segment-shaped trajectory section is arranged in a manner offset by the first rotation angle range relative to a minimum rotation angle position of the first helix-segment-shaped trajectory section in the rotation direction, or
wherein the minimum rotation angle position of the first helix-segment-shaped trajectory section is arranged in a manner offset by the second rotation angle range relative to the minimum rotation angle position of the second helix-segment-shaped trajectory section in the rotation direction.

13. The method of claim 10, further comprising:
obtaining a first part of the second data set with a second radiation spectrum that is different than a first radiation spectrum used for obtaining a first part of the first data set.

14. The method of claim 10, further comprising:
recording the first data set only on first helix-segment-shaped trajectory sections that run in a first rotation direction, recording the second data set only on second helix-segment-shaped trajectory sections that run in a rotation direction that is opposite to or in the same direction as the first rotation direction, or recording the first data set only on first helix-segment-shaped trajectory sections that run in the first rotation direction and recording the second data set only on second helix-segment-shaped trajectory sections that run in the rotation direction that is opposite to or in the same direction as the first rotation direction.

15. The method of claim 10, further comprising:
activating a first beam source when a midperpendicular of a first sensor surface of a first detector is aligned parallel to the first helix-segment-shaped trajectory section; and
activating a second beam source when a midperpendicular of a second sensor surface of a second detector is aligned parallel to the second helix-segment-shaped trajectory section.

16. The method of claim 10, wherein performing the first scan comprises:
carrying out the first scan when a midpoint of a sensor surface of a first detector is displaced relative to a central ray of a beam of a first beam source by half a detector width in a rotation direction or by half the detector width opposite to the rotation direction, carrying out the first scan when the midpoint of the sensor surface of the first detector is displaced relative to a central ray of a beam of the first beam source by half the detector width in a direction of the first helix-segment-shaped trajectory section or the tomography, or carrying out the first scan when the midpoint of the sensor of the first detector is displaced relative to the central ray of the beam of the first beam source by half the detector width in the rotation direction or by half the detector width opposite to the rotation direction and when the midpoint of the sensor surface of the first detector is displaced relative to the central ray of the beam of the first beam source by half the detector width in the direction of the first helix segment shaped trajectory section.

* * * * *